United States Patent [19]

Gralnick

[11] Patent Number: 5,486,361
[45] Date of Patent: Jan. 23, 1996

[54] HYBRIDOMAS AND MONOCLONAL ANTIBODIES THAT SPEIFICALLY BIND TO GPIB ON PLATELETS AND INHIBIT THE BINDING OF THROMBIN TO PLATELETS

[75] Inventor: Harvey R. Gralnick, Kensington, Md.

[73] Assignee: The United States of America as represented by the Department of Health and Human Services, Washington, D.C.

[21] Appl. No.: 140,412

[22] Filed: Oct. 25, 1993

[51] Int. Cl.⁶ .................... A61K 39/395; C07K 16/28; C12N 5/20
[52] U.S. Cl. .................... 424/144.1; 424/143.1; 435/240.27; 435/172.2; 435/70.21; 435/72; 530/388.22; 530/388.7
[58] Field of Search .................... 530/388.22, 388.7; 435/240.07, 172.2, 70.21, 7.2; 424/85.8, 144.1, 143.1

[56] References Cited

PUBLICATIONS

Harris et al. Tibtech 11:42–44, 1993.
Tanaka et al. Microbiol. Immunol. vol. 29 (10):959–972, 1985.
Harlow et al. "Antibodies A Laboratory Manual" Cold Spring Harbor Laboratory 1988, p. 287.
Yamamoto et al., Thrombosis Research, vol. 39, No. 6, pp. 751–759 (1985).
Yamamoto et al. Thrombosis and Haemostasis, vol. 55 (2), pp. 162–167 (1986).
Katagiri et al., Thrombosis and Haemostasis, vol. 63 (1), pp. 122–126 (1990).
Yamamoto et al., Blood, vol. 77, No. 8, pp. 1740–1748 (1991).
Ruan et al., "A Monoclonal Antibody to Human Platelet GPIb Inhibited Both Ristocetin–and Collagen–Induced Aggregation", INSERM Symposium, No. 27, pp. 59–68 (1986).
DeMarco et al., The Journal of Biological Chemistry, vol. 266, No. 35, pp. 23776–23783 (1991).
Mazurov et al., Thrombosis Research, vol. 62, No. 6, pp. 673–684 (1991).

Primary Examiner—Paula K. Hutzell
Attorney, Agent, or Firm—Knobbe, Martens, Olson & Bear

[57] ABSTRACT

Monoclonal antibodies which specifically bind to glycoprotein Ib are described. These antibodies completely inhibit the binding of thrombin to platelets, thereby totally inhibiting the activation of platelets by thrombin. The antibodies also completely inhibit platelet aggregation and also significantly inhibit adhesion of platelets to a subendothelial arterial surface in an ex vivo model system.

9 Claims, 6 Drawing Sheets

HYBRIDOMAS AND MONOCLONAL ANTIBODIES THAT SPEIFICALLY BIND TO GPIB ON PLATELETS AND INHIBIT THE BINDING OF THROMBIN TO PLATELETS

BACKGROUND OF THE INVENTION

1. Field of the Invention

The invention is related to monoclonal antibodies which interact with platelet cells to inhibit various functions associated with platelet activation. The principal activity demonstrated by the monoclonal antibodies of the present invention is inhibition of the binding of thrombin to the glycoprotein Ib on the surface of the platelet cells.

2. Description of the Related Art

Various articles of the scientific and/or patent literature are cited throughout this document. Each of the articles referred to are hereby incorporated in their entirety by such reference.

The essential functions of platelets involve their response to a variety of stimuli. One of the most important physiologic stimuli is alpha thrombin, a coagulation serine protease, derived from prothrombin by cleavage by coagulation factor Xa. Thrombin plays a key role in blood coagulation and thrombosis (pathological coagulation). Thrombin is a central bioregulatory enzyme in hemostasis. It catalyzes the conversion of fibrinogen to fibrin and is responsible for the activation of coagulation factors V, VIII and XIII. Thrombin may also interact with blood vessel walls causing vasoconstriction and may even mediate leukocyte adherence.

Thrombin is the most potent physiologic stimulus which induces platelet activation. The reaction of thrombin with platelets represents an unusual agonist-receptor interaction. Although stimulation of platelets requires the catalytic activity of thrombin, a major protein, the glycoprotein Ib (GPIb), has been isolated on the platelet surface to which thrombin binds. High affinity thrombin binding to GPIb induces platelet activation; this includes platelet shape change, ADP and serotonin secretion, alpha granule release, lysosomal release, the conversion of arachidonic acid to thromboxane A2 and irreversible platelet aggregation. Thromboxane A2 acts as a potent vasoconstrictor and causes aggregation of platelets.

The role of thrombin in arterial thrombosis and in thrombolytic therapy has been clearly defined. Thrombin causes platelet activation and aggregation which is resistant to conventional thrombolytic therapy. Thus, any agent which could interfere with high affinity thrombin binding to the GPIb on the platelet would be an important tool in treating patients with acute arterial thrombosis and could be efficacious in ameliorating the effects of thrombin in arterial thrombus formation and the resultant resistance of arterial thrombi to thrombolytic therapy.

Monoclonal antibodies have been identified which inhibit platelet functions induced by ristocetin or thrombin. One such antibody, TM-60, inhibits binding of von Willebrand factor to platelets in the presence of ristocetin and inhibited the release of adenosine diphosphate (ADP) by thrombin. The authors show that this antibody immunoprecipitates GPIb. It is important to note that this antibody has very little effect on thrombin induced platelet aggregation as shown in Thrombosis Research, volume 39, page 751–759, 1985. The antibody totally inhibited von Willebrand factor binding to platelets. No data was shown concerning binding of thrombin to platelets. In a subsequent publication in Thrombosis and Hemostasis, volume 55, pages 162–167, 1986, the authors showed that there was a thrombin binding site on human platelet GPIb. The authors do not disclose that inhibition of binding of thrombin to GPIb is mediated by their antibody and gave no further functional information concerning this antibody. In another publication in Thrombosis and Hemostasis, volume 63, pages 122–126, 1990, the authors showed data concerning the ability of the TM-60 antibody to inhibit platelet aggregation induced by ristocetin and thrombin. A subsequent paper in Blood, volume 77, pages 1740–1748, 1991 showed that this antibody can only inhibit approximately 50% of high affinity thrombin binding to the platelet.

Another monoclonal antibody to human platelet GPIb, designated antibody SZ-2, inhibited both ristocetin- and collagen- induced aggregation of platelets (C. Ruan et al., in *Monoclonal Antibodies and Blood Platelets*, INSERM Symposium No. 27, pp. 59–68, ed. J. L. McGregor, c. 1986 by Elsiver Science Publishers BV.). A third antibody to GPIb is designated VM 16d and blocks thrombin-induced platelet aggregation at low doses of thrombin, 0.05 u/ml. This antibody recognized a site on the GPIb; however, the authors did not demonstrate that this antibody inhibited high affinity binding of thrombin to platelets nor did they show that their antibody could inhibit thrombin-induced changes in calcium flux or ADP release (C. Ruan et al., Thrombosis Research 62:673–684 (1991)). Another antibody which modifies alpha thrombin function was described by DeMarco (DeMarco et al., J. Biol. Chem. 266:23776–23783 (1991)). This antibody, designated LJ-Ib10, inhibits high affinity thrombin binding to platelets, but does not interfere with the moderate to low affinity binding of thrombin to platelets. Thus, LJ-Ib10 is able to inhibit at most only 50% of the total measurable thrombin binding to platelets. Interference of thrombin binding to platelets by LJ-Ib10 results in decreased fibrinogen binding to platelets and also inhibits the thrombin-mediated calcium flux across the platelet membrane and release of ADP from the cells. The antibody LJ-Ib10 only partially inhibited thrombin-induced platelet aggregation.

The antibody F124H12 (4H12), described in the present application, is similar to the LJ-Ib10 antibody, but demonstrates advantageous properties over that and the other previously described antibodies to GPIb. 4H12 completely inhibits the high affinity binding of thrombin to GPIb, as shown for LJIb-10. As a result, 4H12 completely inhibits the binding of fibrinogen to platelets that results from thrombin activation of the cells. 4H12 also completely inhibits the other physiologic responses of platelets to thrombin. Platelets incubated with 4H12 prior to thrombin exposure retain their unactivated shape, do not exhibit a flux of calcium across the membrane and do not release ADP, serotonin, lysosomes or alpha granules, do not convert arachidonate to thromboxane, and most importantly, the platelets do not aggregate.

SUMMARY OF THE INVENTION

The invention is characterized by the example of the monoclonal antibody 4H12, which specifically binds to the α chain of the GPIb. By means of this interaction, the antibody totally inhibits the binding of thrombin to normal human platelets.

The antibody 4H12 has also been used in studies of the role played by thrombin in maintaining the adhesion of platelets to subendothelial surfaces in the vascular system. 4H12, either as intact antibodies, or as Fab or (Fab')$_2$ fragments, inhibits platelet adhesion to subendothelial surfaces at high shear rates. This inhibition occurs despite the observation that 4H12 does not inhibit ristocetin- or botrocetin-induced binding of von Willebrand factor to platelet cells.

Thus, this antibody has, by in vitro and ex vivo studies, an excellent potential for being an effective antithrombotic agent by i) inhibiting thrombin binding to platelets, and ii) by inhibiting platelet adhesion to subendothelial surfaces.

BRIEF DESCRIPTION OF THE DRAWINGS

FIG. 5A shows the result of a control experiment using the irrelevant antibody 122C11. FIG. 5B shows the result obtained using antibody 4H12. ( - - - , ATP release; —, platelet aggregation)

DETAILED DESCRIPTION OF THE INVENTION

Figure 1:
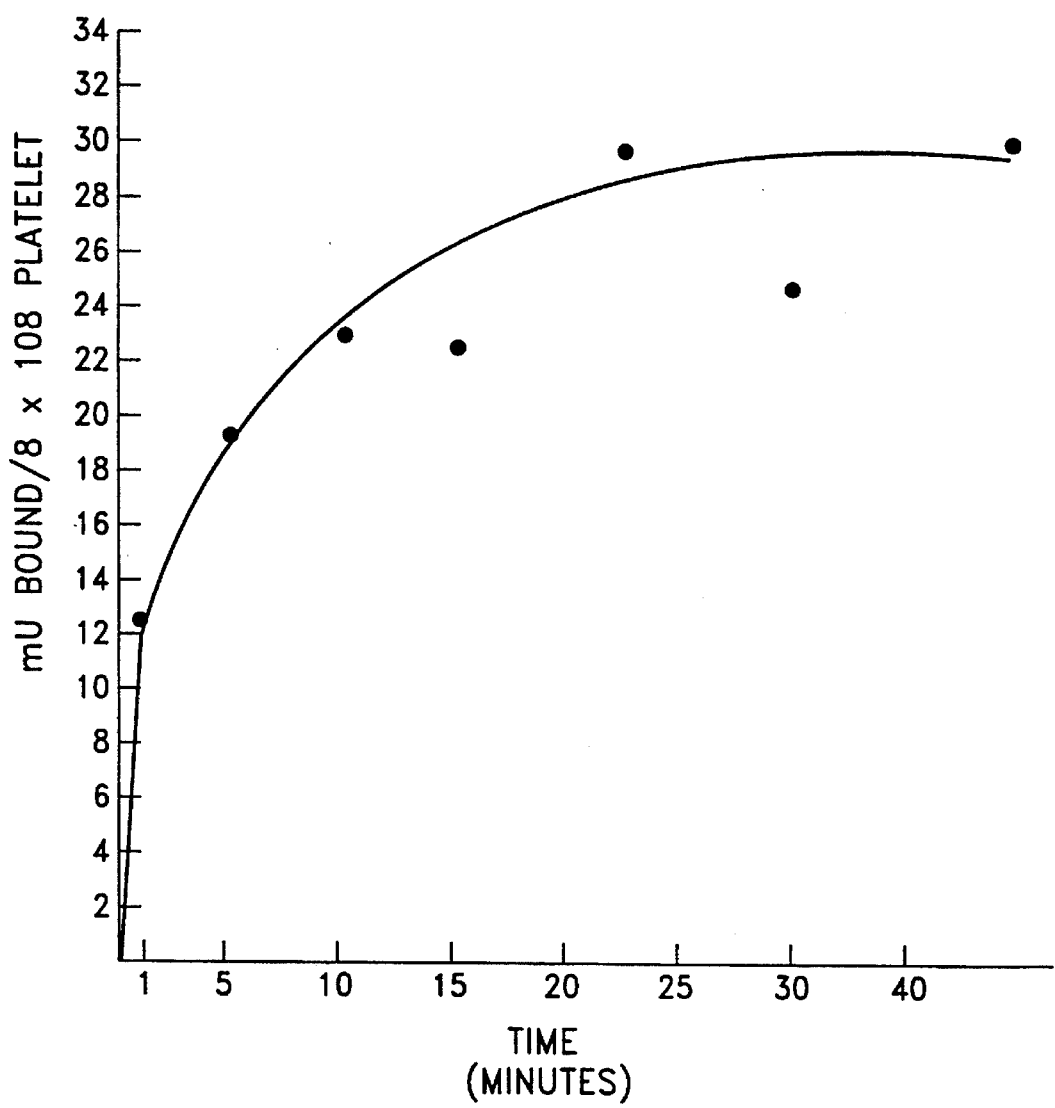
FIG. 1 shows the time course of binding of human alpha thrombin to platelets purified free of plasma proteins.

The 4H12 antibody is important in inhibiting the interaction of platelets with thrombin. The interaction of platelets with thrombin result in a platelet shape change, release of alpha granule constituents and the expression of adhesive proteins on the surface, dense body release reaction, platelet aggregation, and platelet adherence to the subendothelial surface; however, the antibody 4H12 inhibits all of these reactions. These reactions are of central importance in the formation of thrombi on areas of diseased blood vessel surface, in areas of thrombin formation or in areas of high shear force such as a partial obstruction of a coronary artery. In vitro, the antibody 4H12 totally interrupts the sequence of events leading to platelet activation that are mediated by thrombin binding and thus can inhibit the effects of thrombin on platelet release and platelet aggregation. This capability has been explored in flowing and static systems. This antibody has the ability to totally inhibit thrombin interaction with platelets and the effects of thrombin on platelets. This presents a major advance in the field of monoclonal antibodies which inhibit platelet function. It has been postulated and proven that thrombin is generated in areas of thrombosis. Thrombin has a high affinity to bind to platelet GPIb and to cause the reactions described above. The antibody 4H12 has the ability to totally inhibit the effects of thrombin on human platelets. Thus it could be used in a clinical setting of angina pectoris, unstable angina, post acute myocardial infarction, in the presence of mural thrombi, in the presence of cerebral thrombi and large vessel venous thrombosis. This antibody which inhibits not only all of the functions of thrombin on human platelets, but also inhibits platelet adhesion and platelet thrombi generation on subendothelial surface, and thus is potentially an important adjuvant in the treatment of human thromboembolic disease.

The antibody 4H12 displays the following characteristics which have not been demonstrated by previous monclonal antibodies:

i) inhibition of nanomolar concentrations of thrombin to platelets;

ii) total inhibition of thrombin-induced platelet aggregation;

iii) inhibition of >90% of thrombin-induced Von Willebrand factor or fibrinogen binding to platelets;

iv) inhibition of platelet adhesion to the subendothelial layer of arterial walls under shear flow.

EXAMPLE I

Isolation of Hybridomas Secreting Antibodies Which Inhibit Thrombin Binding to Platelets In order to obtain hybridomas which secreted antibodies that inhibit the binding of thrombin to platelets, mice were immunized with purified human platelets, separated from human plasma on arabinogalactan gradients. After six weeks, spleens were removed and the cells dissociated in culture. The immunized spleen cells were hybridized with mouse myeloma cells (SP2-O-Ag14) and distributed in microtiter dishes in the manner well-known in the art. Cultures which demonstrated proliferative growth were cloned by a limiting dilution method. Two separate immunization and fusion experiments were performed. Thus established hybridoma cell lines were grown in the, peritoneal cavity of BALB/c mice and the ascites fluid was obtained therefrom.

Samples of ascites fluid from 250 clones pooled from both fusions were screened by incubating $8\times10^7$ arabinogalactan purified human platelets with 25–50 µl of ascites fluid in a total volume of 0.4 ml of buffer. To this mixture, $1\times10^4$ cpm of $^{125}I$ radiolabelled thrombin were added. The samples were washed to remove unbound thrombin and the amount of radioactivity bound to the cell fraction was quantitated using a gamma counter (TRACOR Analytic).

Of the 250 clones screened, two hybridomas were found to secrete antibodies that inhibited thrombin binding to platelets by more than 25%. The two hybridomas are designated F124H12 (called hereinafter 4H12) and F81A11 (called hereinafter 1A11). The hybridoma 4H12 was deposited under the terms and conditions of the Budapest Treaty at the American Type Culture Collection, 12301 Parklawn Dr., Rockville, Md. on Feb. 7, 1992 and was assigned the accession number HB 10972.

The inhibition of thrombin binding to platelets by antibody 4H12 was examined in more detail. FIG. 1 shows a time course of the binding of thrombin to arabingalactan purified human platelets. $^{125}I$-labelled thrombin was added to the platelets in a modified HEPES buffer, pH 7.35. Half-maximal binding occurs within one minute after the addition of thrombin to purified platelets and reaches saturation at 20 to 25 minutes after the addition of thrombin.

Figure 2:
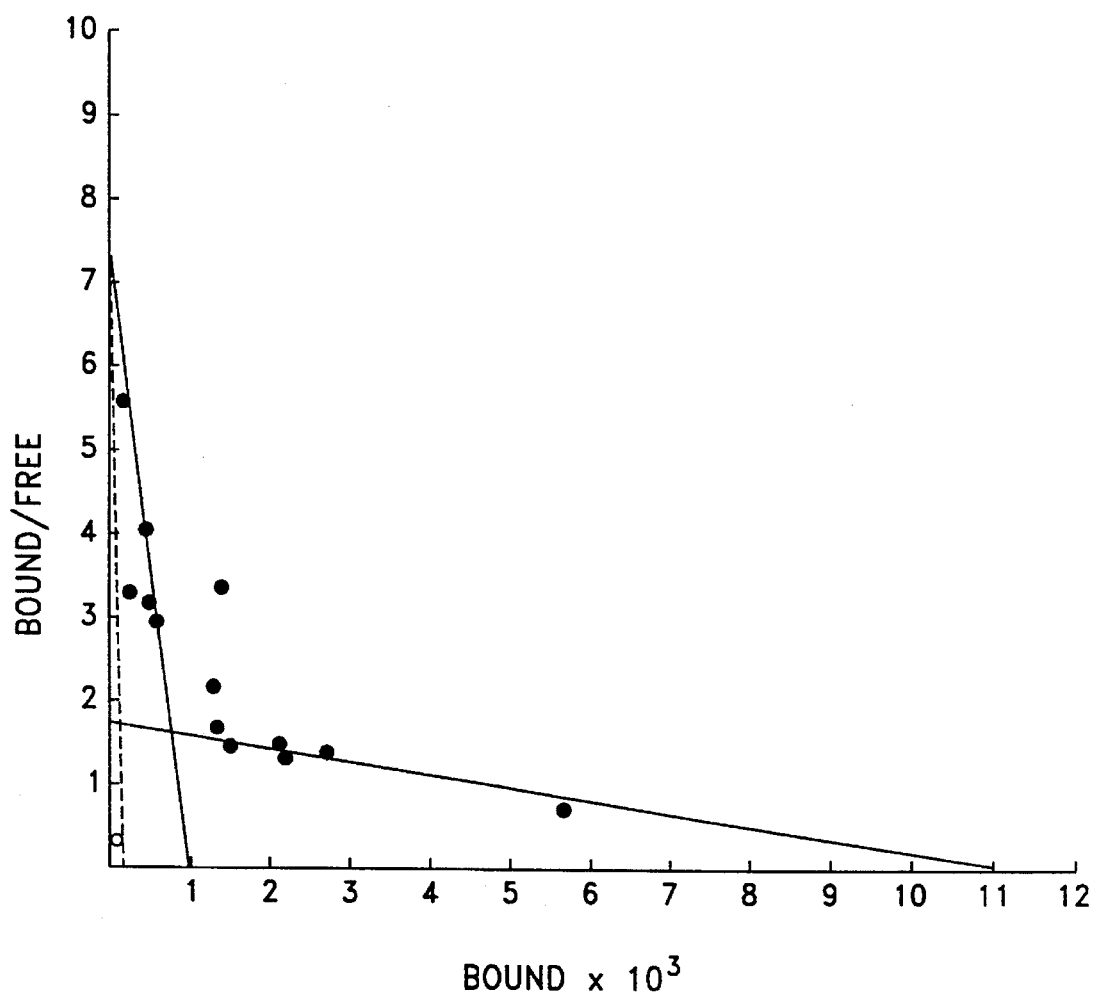
FIG. 2 illustrates a Scatchard analysis of thrombin binding to human platelets purified free of plasma proteins.

FIG. 2 is a Scatchard analysis of binding of thrombin to human platelets. Platelets ($8\times10^7$) were titrated with increasing amounts of thrombin (0.4 µM to 1.23 mM). This analysis demonstrates the existence of two different binding sites for thrombin on the platelet surface.

The solid lines represent the binding isotherms calculated by the LIGAND computer program. One asymptote defines a class of binding sites of high affinity and low capacity with approximately 1,000 receptors with a kD of 3 nM. The second asymptote depicts a second class of receptors of low affinity and high capacity.

Figure 3:
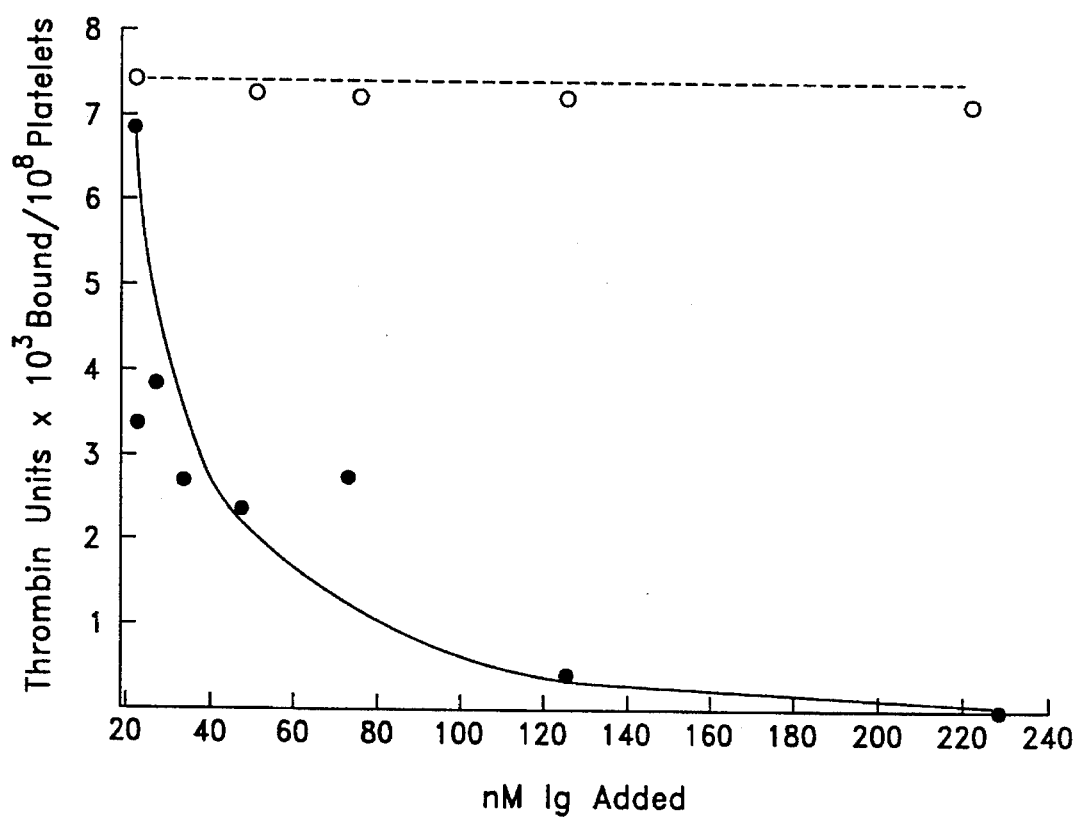
FIG. 3 illustrates the results of a study showing the complete inhibition of high and partial inhibition of moderate affinity thrombin binding to purified platelets by monoclonal antibody 4H12.

Inhibition of thrombin binding by antibody 4H12 was investigated by adding increasing amounts of antibody to the platelets prior to thrombin addition. ($8\times10^7$ cells, 0.1 U/ml thrombin) FIG. 3 shows the effect of antibody 4H12 on thrombin binding to platelets. A dramatic reduction in thrombin binding is demonstrated upon incubation of the platelets with antibody 4H12. In contrast, incubation of the platelets with an irrelevant control antibody does not influence thrombin binding to platelets. The dotted line close to the origin in FIG. 2 shows a Scatchard analysis of the inhibition of the binding of thrombin to platelets by antibody 4H12. To mixtures otherwise identical to the previously described Scatchard analysis, 50 µg of antibody 4H12 were added. All of the high affinity binding sites are inhibited by the monoclonal antibody, and 50–70% of the moderate affinity sites are inhibited.

EXAMPLE III

Immunoprecipitation of the Antigen Recognized by Antibody 4H12

Figure 4:
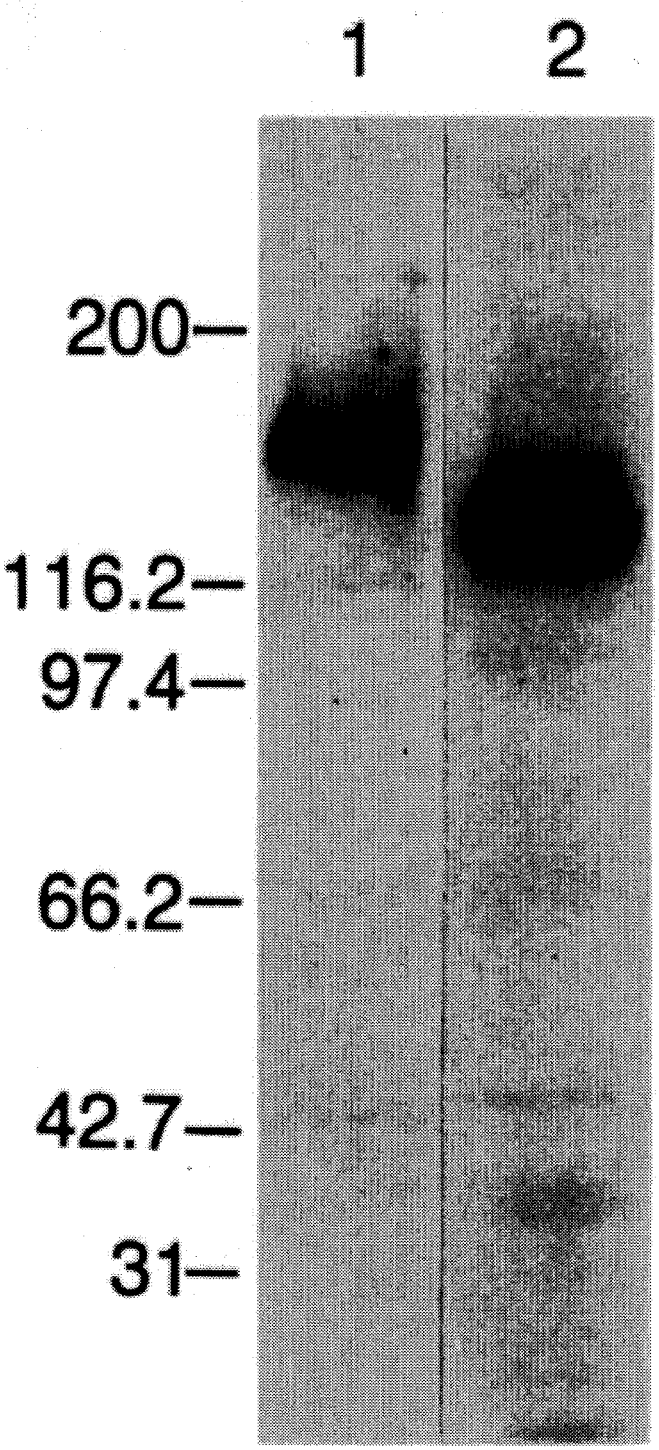
FIG. 4 shows the immunoprecipitation of the platelet membrane glycoprotein GPIb by the antibody 4H12.

The identity of the antigen on the platelet surface that is recognized by the antibody 4H12 was investigated by immunoprecipitation of solubilized platelet membranes using the antibody. Platelet membrane proteins were radiolabelled and solubilized as described by Coller et al. (Coller et al., J. Clin. Invest. 72:325–338 (1983)). Immunoprecipitation was performed as described by Coller et al. (id.), using 100 µg of antibody complexed to protein A-Sepharose. The immunoprecipitated proteins were analyzed by SDS-PAGE under both reducing conditions (i.e. dithiothreitol in the sample buffer) or non-reducing conditions. FIG. 4 shows the results of this analysis.

In lane 1 is the glycoprotein which is immunoprecipitated in a nonreduced state. This protein has a molecular weight of 172 kD and after reduction using dithiothreitol (lane 2) it has a molecular weight of approximately 143 kD (GPIbα). A small band is observed at approximately 37 kD which is the GPIbβ.

EXAMPLE IV

Inhibition of Platelet Aggregation and ATP Release Induced by Thrombin and by Ristocetin The ability of the antibodies 4H12 and 1A11 to inhibit platelet aggregation induced by thrombin and ristocetin was assayed as follows:

Human platelets were purified on LAREX gradients. The platelets were separated from all other cellular elements and plasma proteins by centrifugation on a discontinuous gradient, 10%–20% LAREX. The platelets were washed once and then suspended in phosphate buffered saline (PBS). The platelets were diluted in buffer to a count of $2\times10^5$ cells/µl. 400 µl of purified platelets were placed in a test tube to which varying concentrations of monoclonal antibody was added. The monoclonal antibody concentration varied from 0.05 µg/ml to 50 µg/ml. The antibody and platelets were incubated for 5 minutes, at which time thrombin was added to a concentration of 0.01 U/ml. The aggregation curve was observed for at least 7 minutes at 37° C. As a control for these studies, PBS was added in place of the monoclonal antibody solution. The turbidity value observed in the control reaction was considered to be 100% aggregation. Also, a sample containing PBS in place of monoclonal antibody was incubated at 37° C. for 7 minutes, followed by the addition of thrombin. The value obtained in this "blank" experiment was considered 0% aggregation. The reduction in aggregation attributable to the incubation with the antibody is defined as the percentage of reduction in aggregation compared to the no antibody sample. Experiments using both intact monoclonal antibodies and F(ab)'$_2$ fragments thereof were performed.

Inhibition of thrombin-induced aggregation was assayed at 0.1 unit/ml thrombin, while inhibition of ristocetin-induced aggregation was assayed at 0.5 mg/ml ristocetin.

In some experiments, inhibition of ADP release from platelets stimulated with thrombin or ristocetin was studied using the luciferin-luciferase reagent (Sigma Chemical Co, St. Louis, Mo.) and the Chrono-Lumi aggregometer, per the manufacturers instructions.

Figure 5A:
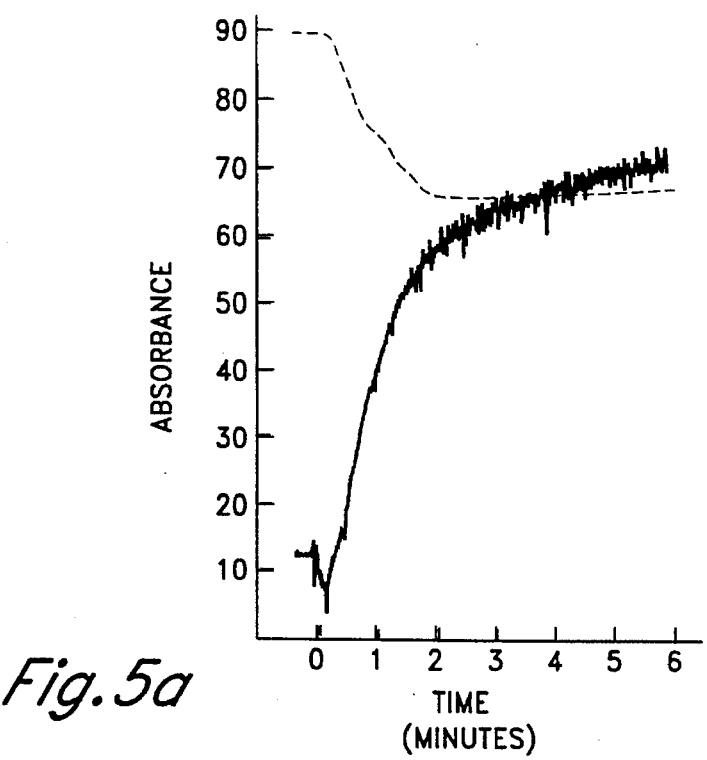
FIG. 5A and 5B shows inhibition of thrombin stimulation of ATP release from platelets and platelet aggregation by antibody 4H12.

FIG. 5 illustrates the effect of antibody 4H12 on the thrombin-induced aggregation of platelets and also shows that 4H12 inhibits ATP release from platelets upon stimulation by thrombin. In FIG. 5A, results using an irrelevant, control antibody 122C11, are shown.

Figure 5B:
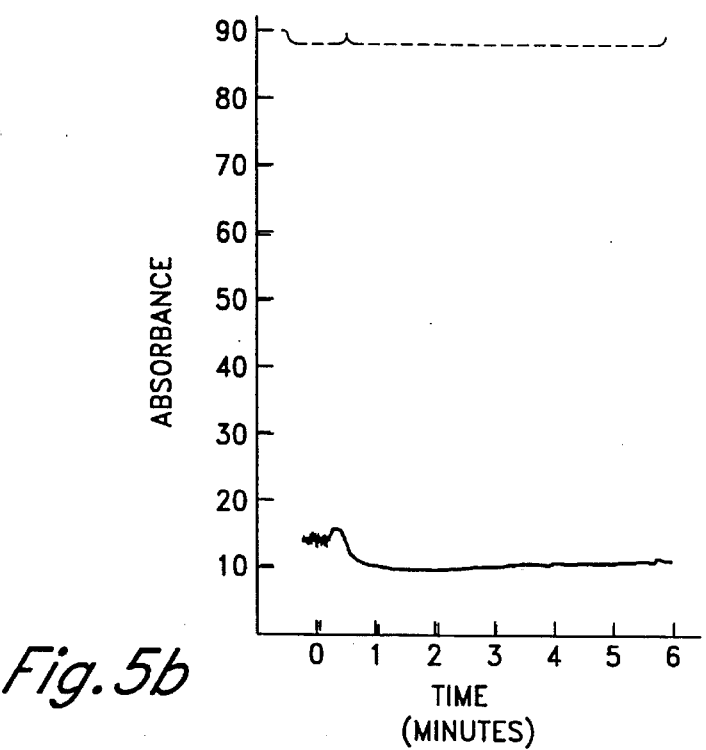
Figure 6A:
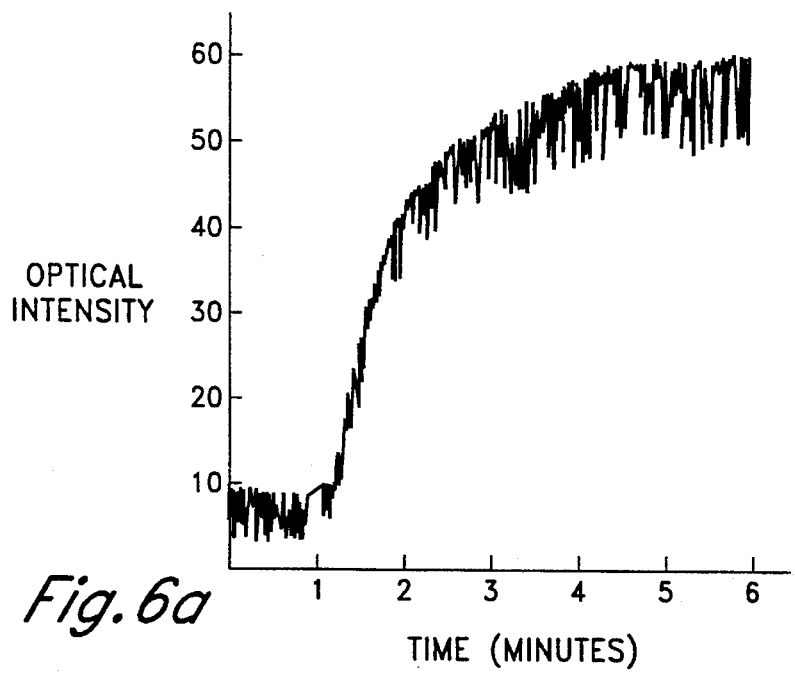
FIG. 6A–6D show the dose dependence of inhibition of thrombin-induced platelet aggregation by the antibody 4H12 (FIG. 6A, 0 µg/ml antibody, FIG. 6B, 25 µg/ml, FIG. 6C, 3.35 µg/ml, FIG. 6D, 0.87 µg/ml)
Figure 6B:
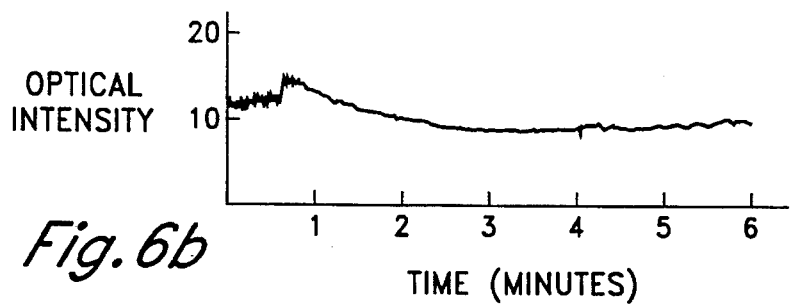
Figure 6C:
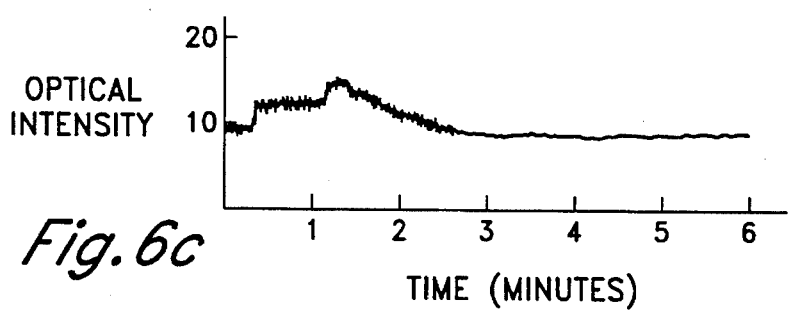
Figure 6D:
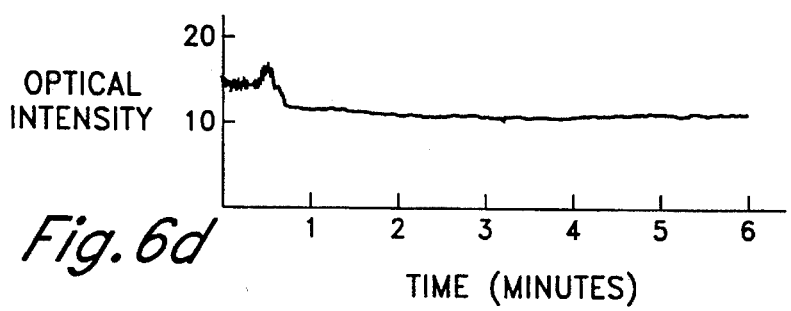

FIG. 5B illustrates the same experiment performed using the antibody 4H12. The total inhibition of both ATP release and platelet aggregation by antibody 4H12 is clearly evident from comparison of the two figures.

FIG. 6 illustrates the dose-dependence of the inhibition of platelet aggregation by antibody 4H12. Aggregation of $8\times10^7$ platelets stimulated by 0.1 unit of thrombin was assayed as described above using various amounts of the antibody. Total inhibition of platelet aggregation was observed at the lowest antibody dose tested, 0.87 µg/ml.

The $IC_{50}$ for thrombin-stimulated platelet aggregation was found to be 1.8 µM for antibody 4H12. In a similar manner, the $IC_{50}$ for thrombin-stimulated platelet aggregation for antibody 1A11 was found to be 1.7 µM.

Inhibition of ristocetin-stimulated platelet aggregation was studied in a similar manner. It was found that the $IC_{50}$ for ristocetin-induced platelet aggregation by 4H12 is 46 µM, while antibody 1A11 demonstrates a value of 1.6 µM in the same assay.

EXAMPLE V

Inhibition of Adhesion of Platelets to Subendothelial Matrix Under High Shear by Antibody 4H12

In order to investigate the efficacy of various treatment modalities in inhibiting platelet adhesion to blood vessel walls, an ex vivo model system was developed in our laboratory. The system is a modification of the Baumgartner technique, and is described in detail in Lawrence et al. (J. B. Lawrence et al., J. Clin. Invest, 86:1715–1722 (1990)). Briefly, a section of umbilical cord artery is placed in culture in an apparatus which maintains a laminar flow of the culture medium over the exposed surface of the cells. The endothelial cells are then removed by exposure to air to reveal the subendothelial matrix. Whole blood is then perfused over the vessel wall for 5 minutes at 37° C. at a shear force of $2600^{-1}$ sec in the presence or absence of monoclonal antibody 4H12. At the end of the perfusion the vessel wall is fixed and morphometry is performed. The number of contact platelets, spread platelets and platelet thrombi are identified according to the protocol of Baumgartner et al.

This system is a good representation of the dynamics of the interior of an artery and provides a model system which is predictive of adhesion effects in vivo.

I have used the modified Baugartner model system to investigate the ability of the antibody 4H12 to inhibit platelet aggregation to the subendothelial layer and thrombi formation. It was found that at high shear flow rates, the antibody 4H12, at a concentration of 5 μg/ml, inhibits 31% of platelet adhesion to the endothelial cell layer. Similarly, inhibition of 51% of the adhesion was seen at 10 μg/ml, 56% at 20 μg/ml and 65% at 40 μg/ml. Of great importance, no platelet thrombi were formed on the subendothelial surface in the presence of the antibody.

EXAMPLE VI

Diagnosis of Bernard-Soulier Syndrome

Patients presenting with Bernard-Soulier Syndrome are found to lack all or a part of the GPIb. Accordingly, methods typically employed in the art for immunoassay of cell-surface proteins, such as radioimmunoassay, enzyme-linked immunosorbent assay and flow cytometry of antibody-labelled cells, could be used to aid in the diagnosis of Bernard-Soulier Syndrome. These methods can also be used to identify acquired disorders which modify the GPIb on platelet surfaces, e.g. platelets which have been exposed to subendothelial surfaces or to thrombin would bind less of 4H12 antibody, thus providing an indication of platelet activation. In such a diagnostic test, an observation of a lack of antibody 4H12 binding to platelets from a patient would be taken as indicative of a lack of functional GPIb on the surface of the platelets from the patient, or an indication that platelet have been activated by thrombin or other stimuli.

All of the properties with respect to inhibition of thrombin binding to platelets, inhibition of platelet aggregation, immunoprecipitation of antigen, etc. that are described for the intact antibody 4H12 are similarly displayed by F(ab)'$_2$ fragments of the 4H12 antibody. For example, the IC$_{50}$ for inhibition of thrombin- and ristocetin-induced platelet aggregation by F(ab)'$_2$ fragments of antibody 4H12 are 1.5 μM and >20 μM, respectively. For fragments from antibody 1A11, these values are 1.6 μM and 3.0 μM. F(ab)'$_2$ fragments of antibodies are made by limited proteolysis of the antibody using methods well-known in the art.

The monoclonal antibodies of the present invention can be formulated into pharmaceutical compositions by use of any of the various additives commonly employed in the art. Typical of such additives are carriers and excipients, diluents and the like. For example, the antibodies can be formulated by dilution in a sterile saline solution for administration by injection.

Administration of the antibodies of the present invention can be performed by the routes typical in the art. For the prevention of platelet aggregation in vivo, one of skill in the art would consider that intravenous injection would be an effective route of administration. Dosages to be employed would be expected to be typical for administration of monoclonal antibodies to a patient, in the range of 0.05 to 20 mg/kg as a unit dose. The preparation of monoclonal antibodies for administration by intravenous injection, as well as by many other routes, is considered well-known in the art.

The invention being thus described, various modifications of the materials and methods set forth herein, will be obvious to one of skill in the art. Such modifications are to be considered as within the scope of the invention as set forth in the claims hereinbelow.

What is claimed is:

1. A monoclonal antibody having the characteristics of:
   i) binds to glycoprotein Ibα
   ii) inhibits thrombin binding to platelets at nanomolar concentrations of thrombin;
   iii) completely inhibits thrombin-induced platelet aggregation;
   iv) completely inhibits the high affinity binding of thrombin to GPIb; and
   v) inhibits 50–70% of the moderate affinity thrombin binding sites on platelets.

2. A monoclonal antibody according to claim 1, having the additional characteristics of:
   iv) inhibits >90% of thrombin-induced Von Willebrand factor or fibrinogen binding to platelets;
   v) inhibits platelet adhesion to the subendothelial layer of arterial walls under shear flow.

3. A monoclonal antibody according to claim 2, which is the monoclonal antibody secreted by the hybridoma deposited as HB 10972.

4. A hybridoma which secretes the monoclonal antibody of claim 1.

5. A hybridoma which secretes the monoclonal antibody of claim 2.

6. The hybridoma deposited as HB 10972.

7. A pharmaceutical composition comprising the antibody of claim 1 and a carrier.

8. A pharmaceutical composition comprising the antibody of claim 2 and a carrier.

9. A pharmaceutical composition comprising the antibody of claim 3 and a carrier.

* * * * *